United States Patent [19]

Dorsel

[11] Patent Number: 5,675,443
[45] Date of Patent: Oct. 7, 1997

[54] METHOD AND APPARATUS FOR IMAGING THROUGH A PLANAR, TRANSPARENT SUBSTRATE AT AN OBLIQUE ANGLE

[75] Inventor: Andreas Dorsel, Menlo Park, Calif.

[73] Assignee: Hewlett-Packard Company, Palo Alto, Calif.

[21] Appl. No.: 508,230

[22] Filed: Jul. 27, 1995

[51] Int. Cl.$^6$ ...................................................... G02B 3/00
[52] U.S. Cl. ................................................................ 359/737
[58] Field of Search ...................................... 359/737, 642

[56] References Cited

PUBLICATIONS

"Biophotonics News", Biophotonics International, Jan./Feb. 1995, pp. 28–29.
Fodor, et al., Science, vol. 251, 15 Feb. 1991, pp. 767–773.
Fischer, Robert E., "Practical Optical System Design", Photonics West '95, 7 Feb. 1995.

*Primary Examiner*—Scott J. Sugarman

[57] ABSTRACT

A system for imaging through a tilted plane parallel plate, in which image quality is improved by inserting additional transparent plates between an object that is imaged and the imaging lens, includes at least two plates of preferably identical thickness and material to that of the plate through which the object is imaged. The plates are tilted by appropriate angles around tilt axes that are orthogonal to the optical axis of the lens. The tilt axes themselves are rotated around the optical axis with respect to each other. The invention greatly improves the image quality when imaging through a tilted plane parallel plate. The preexisting optical system remains rotationally symmetric except for the plates inserted therein. Such plane plates are readily manufacturable at reasonable cost, and they require only noncritical alignment within the system.

20 Claims, 9 Drawing Sheets

OBJ: 0.0000 0.0000 DEG

IMA 0.000 0.238 MM

OBJ: 2.3000 0.0000 DEG

IMA 4.024 0.238 MM

OBJ: 4.6000 0.0000 DEG

IMA 0.062 -0.237 MM

OBJ: 6.9000 0.0000 DEG

IMA 0.000 -0.237 MM 5,675,443

METHOD AND APPARATUS FOR IMAGING THROUGH A PLANAR, TRANSPARENT SUBSTRATE AT AN OBLIQUE ANGLE

FIELD OF THE INVENTION

The invention relates to optical systems. More particularly, the invention relates to imaging through a planar, transparent substrate at an oblique angle.

BACKGROUND OF THE INVENTION

Modern optical instrumentation may require that an area of interest is imaged through a transparent, planar medium at an angle that is oblique to the plane surface of the medium. FIG. 1 is a schematic representation of such an imaging system 10 in which a planar, transparent substrate 12 is illuminated by a light source 16 which is placed substantially normal to the surface of the substrate. A detector 14 is positioned at an angle 11 that is oblique to the plane surface of the substrate.

In such imaging system, it is desired to image through the substrate to the substrate back surface 15. This technique has been found useful for analytical instrumentation, such as state of the art DNA analysis systems. Such DNA analysis may be performed using a substrate that includes a high density array of one million or more DNA probes situated on a surface that may be less than 1.28 cm$^2$.

A process referred to as very large scale immobilized polymer synthesis uses a combination of photolithography and solid-state chemical synthesis techniques (see, for example W. C. Holton, HP and Affymetrix Join to Develop DNA Sequencer, Photonics International, pp. 28, 29 (January/February 1995); and S. Fodor, J. L. Read, M. Pirrung, L. Stryer, A. Tsai, D. Solas, Light-Directed, Spatially Addressable Parallel Chemical Synthesis, Science, vol. 251, pp. 767–773 (15 Feb. 1991).

In practice, a light is shone through a computer designed photolithographic mask onto the light sensitive surface of a substrate, such as a glass hybridization chip, to activate specific areas of the chip surface. The chip is then immersed in a solution containing one of four different nucleotides that are present in DNA. The nucleotides react only with the areas of the chip that were light activated. By using a number of cycles, and by varying the mask design and nucleotide sequence that is deposited on the chip, a large number of DNA strands, or probes, can be synthesized simultaneously.

Thus, the chip is in effect a miniature checkerboard of different nucleotide sequences that are anchored to the surface of the chip. DNA identification in a nucleic acid sample is carried out by labeling the sample with a detectable reporter molecule, such as a fluorescent molecule, and reacting the sample with the chip under conditions that allow for specific binding between DNA immobilized on the chip and complementary DNA in the sample.

After the unbound DNA is washed away, the chip is imaged with a laser-based scanning confocal microscope that identifies and records where the remaining sample is bound. Because the sequence of DNA at each array position on the chip is known, computer algorithms can determine the sequence of any bound, fluorescently labeled DNA by knowing the DNA's position.

The chip may be imaged with its processed surface facing toward the microscope objective, i.e. directly imaged, or with its processed surface facing away from the microscope objective, i.e. imaged through the chip. FIG. 1 illustrates that latter case, where the processed surface 15 is imaged through the substrate 12. The substrate is illuminated at an angle that is substantially normal to the substrate surface, for good spot quality. Therefore, it is preferable to minimize reflection and glare by imaging the processed surface of the substrate at an angle that is oblique to the plane surface of the substrate. The reflected light might otherwise, even with wavelength selective filters, overwhelm light signals that are to be detected. It is desirable to provide a low noise system.

FIG. 2a is a view taken parallel to the field line for an imaging system that includes one plate 12, which is the initial plate or substrate. FIG. 2b is a view taken vertical to the field line for the imaging system of FIG. 2a. For purposes of the discussion herein, the term substrate shall also mean the initial plate.

One problem with imaging through a plane parallel substrate, such as a hybridization chip, at an oblique angle (e.g. 45°) with a non-paraxial numerical aperture (NA), e.g. 0.25, is that of aberration contributed to the image by the imaging process. It has been found that imaging through a transparent medium at an angle that is oblique to the plane surface of the medium produces significant blurring. For example, FIG. 3 is a spot diagram for the imaging system of FIGS. 2a and 2b in which the image pattern is asymmetrically dispersed, indicating severe blurring.

R. E. Fischer, *Practical Optical System Design*, Photonics West 95, SPIE's International Symposium on Lasers and Applications, Biomedical Optics, Optoelectronic, Microphotonics, and Electronic Imaging, page 49 (7 Feb. 1995) shows a design that corrects third order astigmatism blur for a plate that is tilted at 45° relative to a point of observation. However, such approach is considered unsatisfactory because, while reasonable correction is provided on-axis for just one point, there is a significant amount of degradation of image quality as imaging occurs away from center of the imaged object.

FIG. 4a is a view taken parallel to the field line for an imaging system that includes two plates, and FIG. 4b is a view taken vertical to the field line for the imaging system of FIG. 4a. As can be seen in FIG. 5, which shows various spot diagrams 50, 51, 52, 53 for the imaging system of FIGS. 4a and 4b, the addition of one plate 40 between the initial plate 12 and the detector 14 does not provide off-center compensation with regard to the observed image. Thus, the addition of one plate within the path of observation does not compensate for aberrations introduced by imaging through a transparent medium at an oblique angle relative to the plane surface of the medium.

It would be advantageous to provide an imaging system in which aberrations due to imaging at an oblique angle relative to a plane surface of a transparent substrate are minimized or eliminated.

SUMMARY OF THE INVENTION

The invention provides a system for imaging through a tilted plane parallel plate, in which image quality is improved by inserting additional transparent plates between an object that is imaged and the imaging lens train. In the preferred embodiment of the invention, at least two plates of preferably identical thickness and material to that of the initial plate which is imaged are so placed. The plates are tilted by appropriate angles around tilt axes that are orthogonal to the optical axis of the lens. The tilt axes themselves are rotated around the optical axes with respect to each other.

The invention greatly improves the image quality when imaging through a tilted plane parallel plate. The preexisting optical system remains rotationally symmetric except for the plates inserted therein. Such plane plates are readily manufacturable at reasonable cost, and they require only noncritical alignment within the system.

BRIEF DESCRIPTION OF THE DRAWINGS

FIG. 2b is a view taken vertical to the field line for the imaging system of FIG. 2a;

FIG. 4b is a view taken vertical to the field line for the imaging system of FIG. 4a;

FIG. 6b is a view taken vertical to the field line for the imaging system of FIG. 6a;

DETAILED DESCRIPTION OF THE INVENTION

The invention provides a system for imaging through a tilted plane parallel plate, in which image quality is improved by inserting additional transparent plates between an object that is imaged and the imaging lens train.

In one preferred embodiment of the invention, at least two plates of preferably identical thickness and material to that of the initial plate which is imaged are so placed. The plates are tilted by appropriate angles around tilt axes that are orthogonal to the optical axis of the lens. The tilt axes themselves are rotated around the optical axes with respect to each other.

Figure 1:
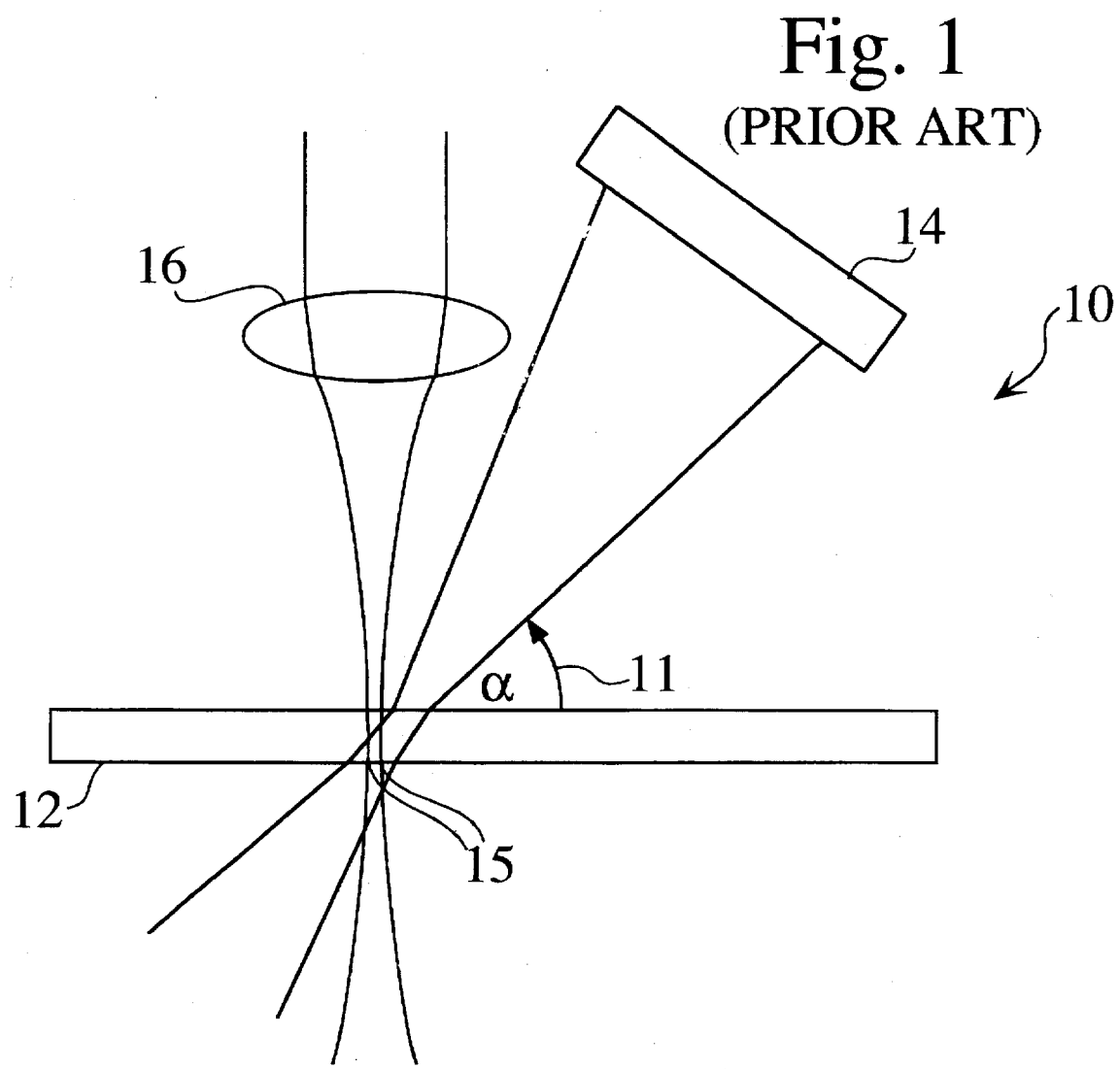
FIG. 1 is a schematic representation of an imaging system in which imaging is through a planar, transparent substrate at an oblique angle.
Figure 2A:
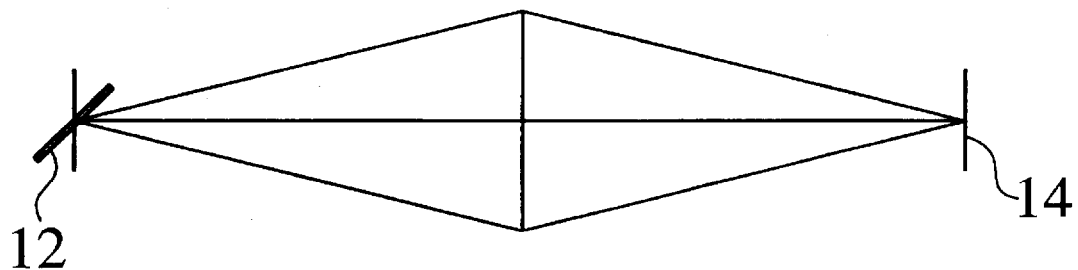
FIG. 2a is a view taken parallel to the field line for an imaging system that includes one plate.
Figure 2B:
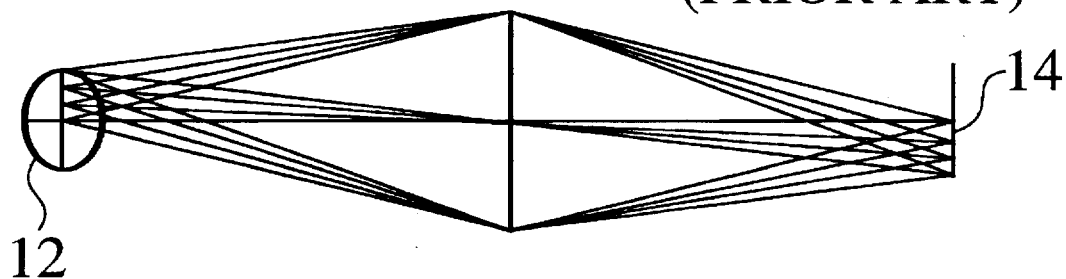
Figure 3:
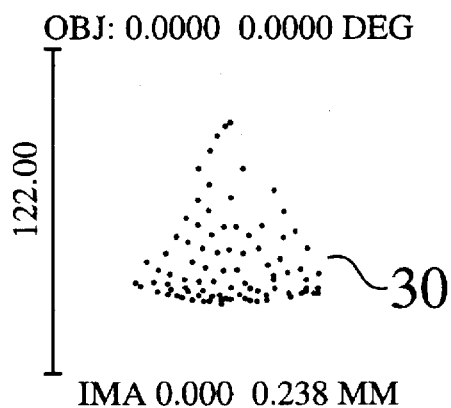
FIG. 3 is a spot diagram for the imaging system of FIGS. 2a and 2b.
Figure 3:
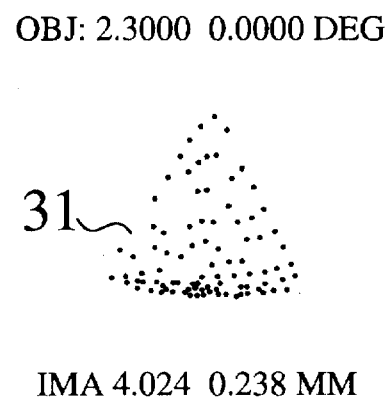
Figure 3:
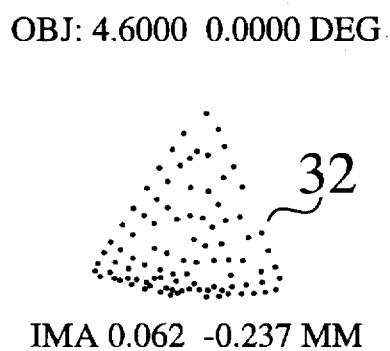
Figure 3:
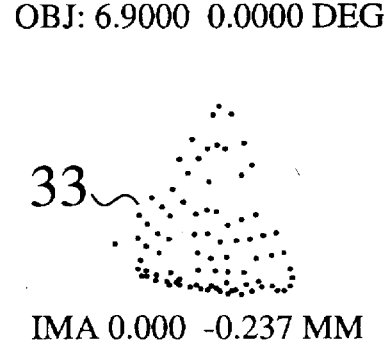
Figure 4A:
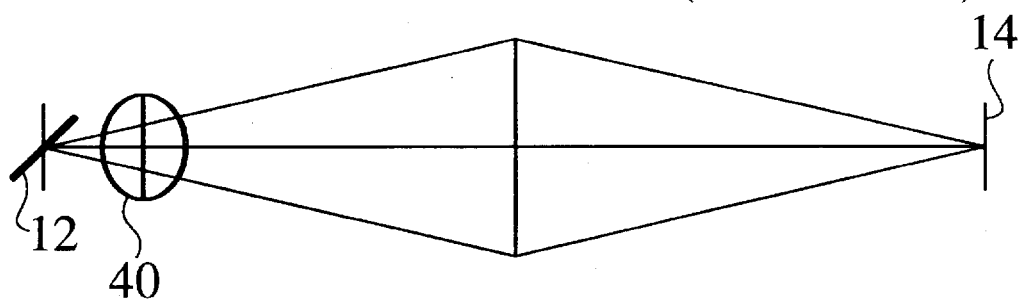
FIG. 4a is a view taken parallel to the field line for an imaging system that includes two plates.
Figure 4B:
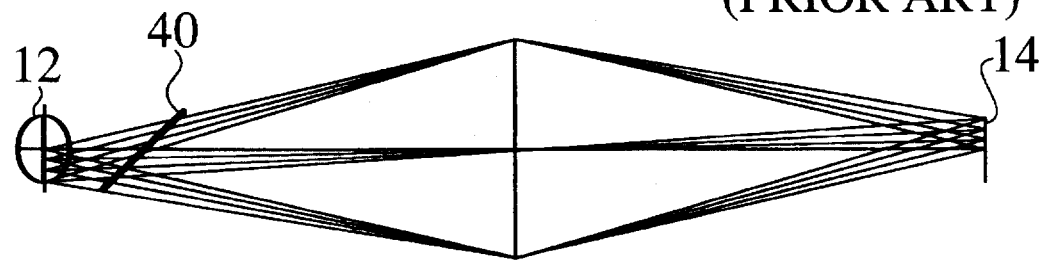
Figure 5:
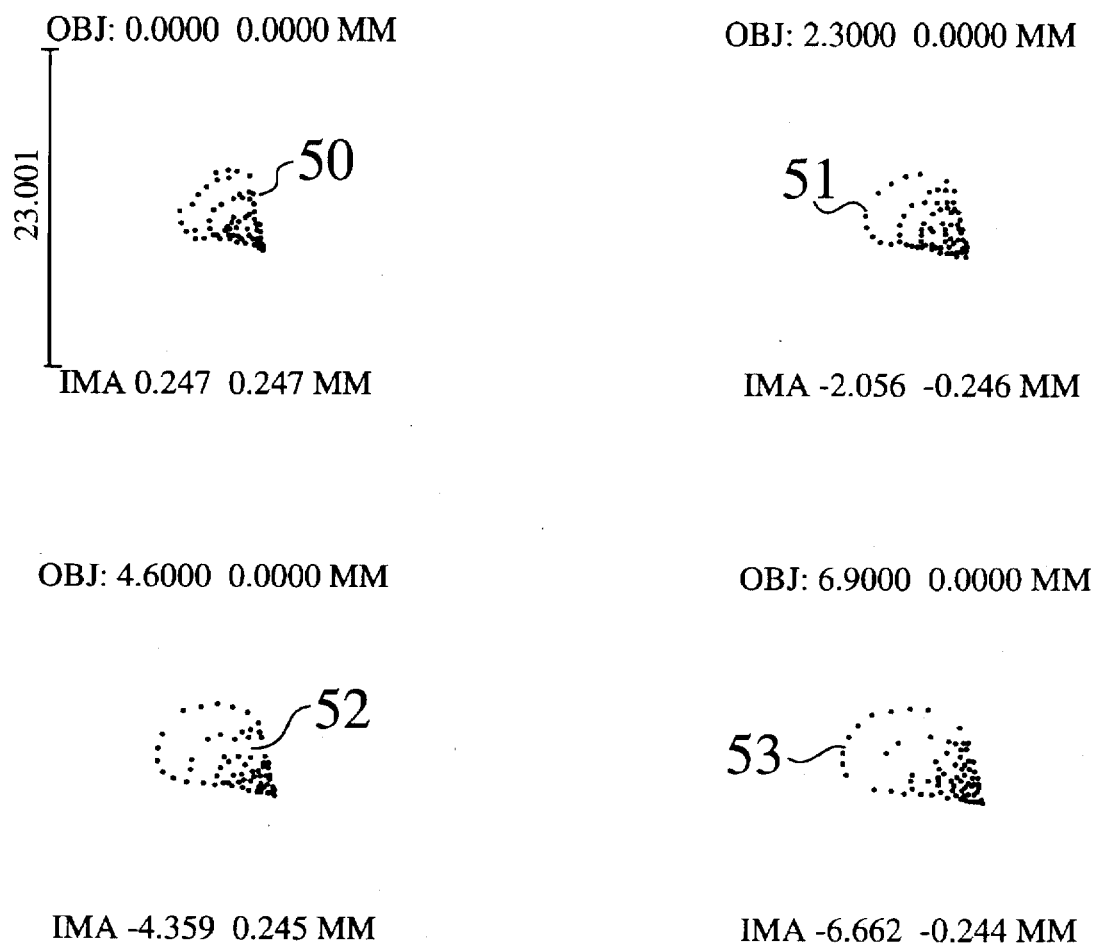
FIG. 5 is a spot diagram for the imaging system of FIGS. 4a and 4b.
Figure 6A:
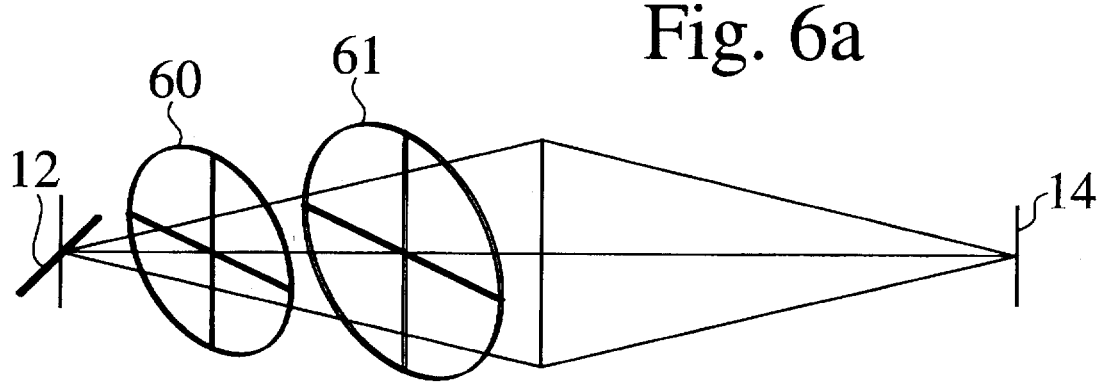
FIG. 6a is a view taken parallel to the field line for an imaging system that includes three plates.
Figure 6B:
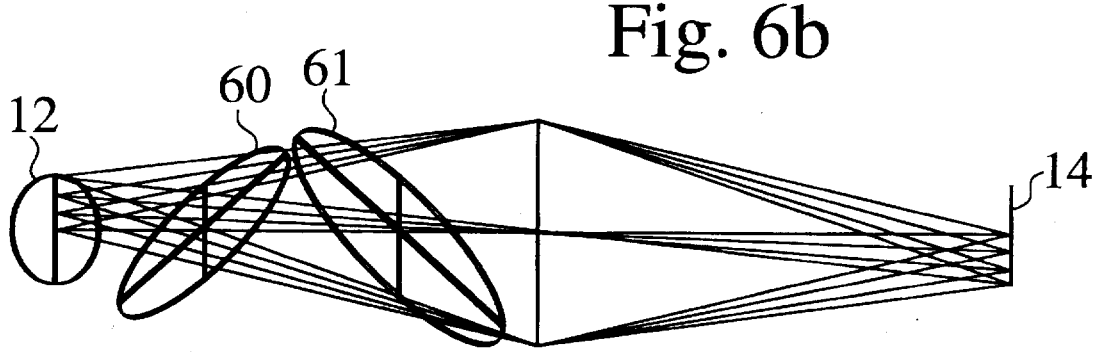

FIG. 6a is a view taken parallel to the field line for an imaging system that includes three plates 12, 60, 61, and FIG. 6b is a view taken vertical to the field line for the imaging system of FIG. 6a. In another equally preferred embodiment of the invention, a number n of plates, preferably three or four plates (including the initial plate that caused the problem) are used. Each plate has the same tilt angle, e.g. 45°, and has a tilt axis that is rotated by $\beta = i*360°/n$ with $i = 0, 1, \ldots, n-1$ around the optical axis with respect to the initial plate. Each of the angles corresponding to the different values of i is used, where $i=0$ is the trivial position of the first plate. The order in which the other angles occur is free.

For example, consider the addition of two plates 60, 61 at 45° (as shown in FIGS. 6a and 6b) with their axes rotated by 120° and 240° relative to the tilt axis of the initial plate, or three of more plates 80, 81, 82 (see FIGS. 8a and 8b) having their tilt axes rotated by 90°, 180°, and 270°. The sign of the rotation angle may be reversed in the example herein for all plates, but not for subgroups of the plates.

While the surface of the initial plate may be of less stringent quality, the requirements for the compensating plates provided in accordance with the invention are more stringent because only a small field on the former is used for imaging a given part of the object, while a large area of the plates is traversed by light rays.

If the refractive index of the compensating plates differs from that of the initial plate, the optimum thickness of the compensating plates is increased for higher refractive index materials and decreased for lower refractive index materials. Good performance is generally achieved if an identical material is used for all plates, i.e. the initial plate and the compensating plates.

If desired, for example due to material cost or to include filter glasses, some of the plates can be made from different materials if appropriate thickness changes are made to the plates to compensate for difference in refractive index. However, this approach may increase the likelihood of problems associated with chromatic effects. For a given material, and thus refractive index, the optimum thickness of the compensating plates can be determined using a lens design program, such as Zemax, which is manufactured by Focus Software of Tucson, Ariz. The plates themselves are available from such vendors as Corning of Corning, N.Y.

The diameter of the compensating plates should increase as the distance of the plates from the initial plate increases because the bundle of rays that is imaged increases in diameter as the distance from the imaged object increases. All of the compensating plates are oriented to the optical axis at the same angle, in this case 45°.

The tilt axes of the compensating plates are normal to the optical axis. The thickness and material of the compensating plates is preferably the same as the thickness and the material of the initial plate.

If desired, variations in thickness may be compensated by changing the glass type of the plates. However, the choice of refraction index is much more limited than the choice of thickness. Therefore, it is preferred to choose a refractive index for the plates first, preferably where each plate has the same refractive index, and then adjust the thickness of each plate as desired.

With a given imaging lens, refocusing is accomplished after insertion of the compensating plates. When thicker plates are used, it may be necessary to reoptimize the imaging lens to correct for any rotationally symmetric aberration that is induced.

The compensating plates discussed above are preferably made of a material having a similar thickness and refractive index as that of the initial plate, and may be made from such materials as BK7, K5, silica, especially low-fluorescent silica. In the preferred embodiment of the invention, the plates are about 40 up to about 100 millimeters in diameter.

The plates do not have to be circular. For example, the compensating plates may be slightly larger in one dimension. It may be preferred in some applications not to have some of the plates circular because some portions of the field would be large enough to require a larger circular plate. While a circular plate is less expensive, a portion of the plate would most likely protrude farther out than is needed. Having noncircular plates reduces the space required to mount the plates.

Figure 7:
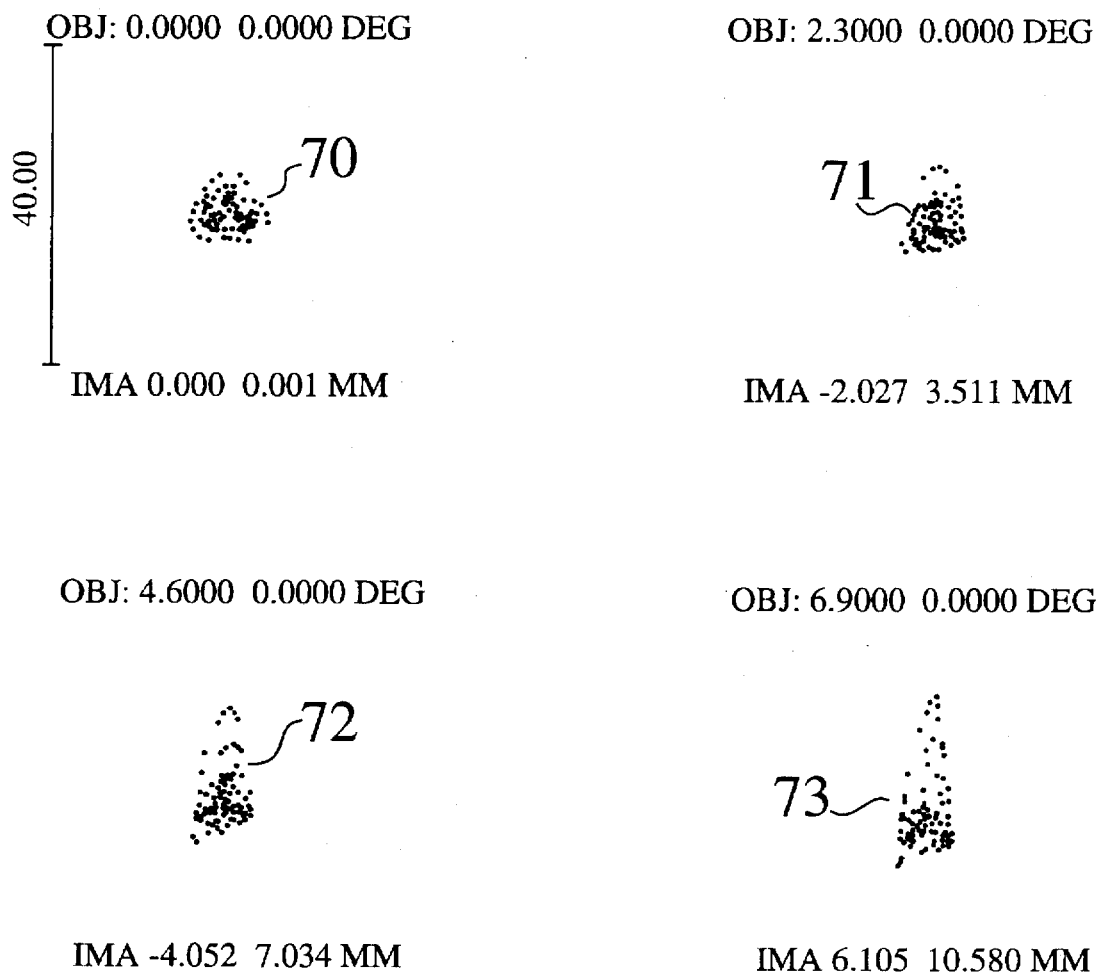
FIG. 7 is a spot diagram for the imaging system of FIGS. 6a and 6b.

FIG. 7 is a spot diagram for the imaging system of FIGS. 6a and 6b. As can be seen, much smaller diameters of spot diagrams 70, 71, 72, 73 are produced when compensating plates are placed in the optical path between the object and the detector.

Figure 8A:
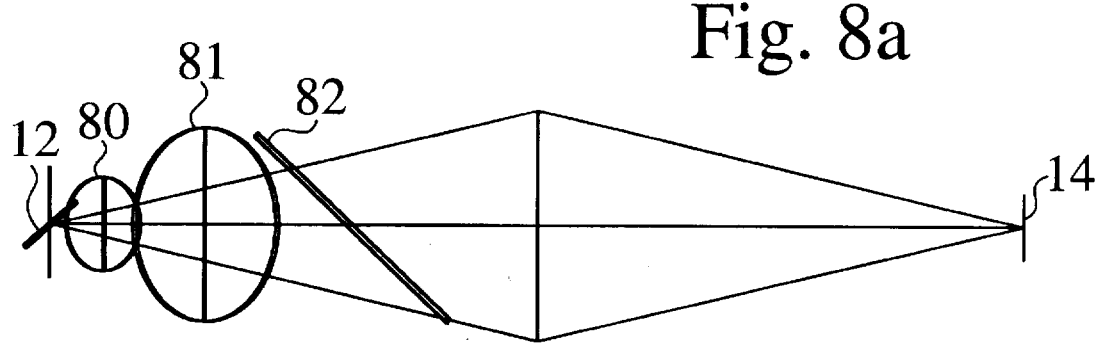
FIG. 8a is a view taken parallel to the field line for an imaging system that includes four plates.
Figure 8B:
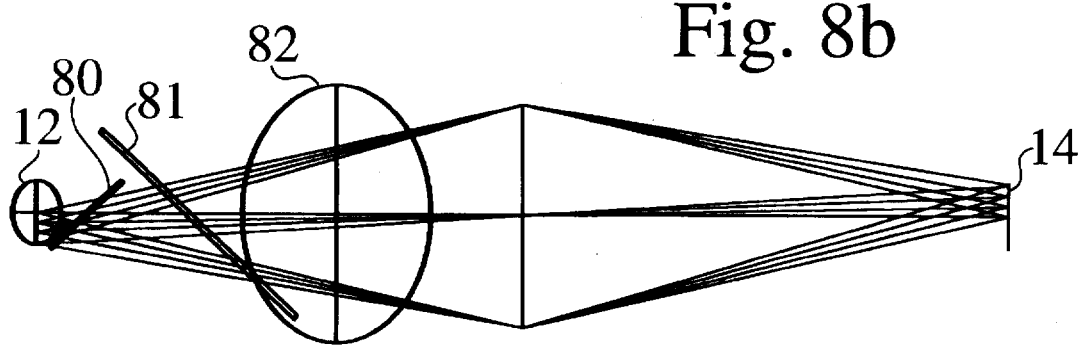
FIG. 8b is a view taken vertical to the field line for an imaging system that includes four plates.

FIG. 8a is a view taken parallel to the field line for an imaging system that includes four plates 12, 80, 81, 82, and FIG. 8b is a view taken vertical to the field line for an imaging system that includes four plates. The main difference between the use of three plates, as shown in FIGS. 6a and 6b, and the use of four plates, as shown in FIGS. 8a and 8b, is that a four plates solution is more expensive. However, performance is also improved considerably in the four plate embodiment of the invention.

In the figure, two pairs of plates are provided, including the initial plate, where the plate pairs are rotated in opposite directions and then rotated the sameamount. The compensating plates have their tilt axes rotated by 90°, 180°, and 270°. In this example, the amount of rotation of each plate relative to the optical axis is always 45°. The order in which the plates are placed in the image path does not matter, as long as the plates cumulatively implement the three different orientations.

Figure 9:
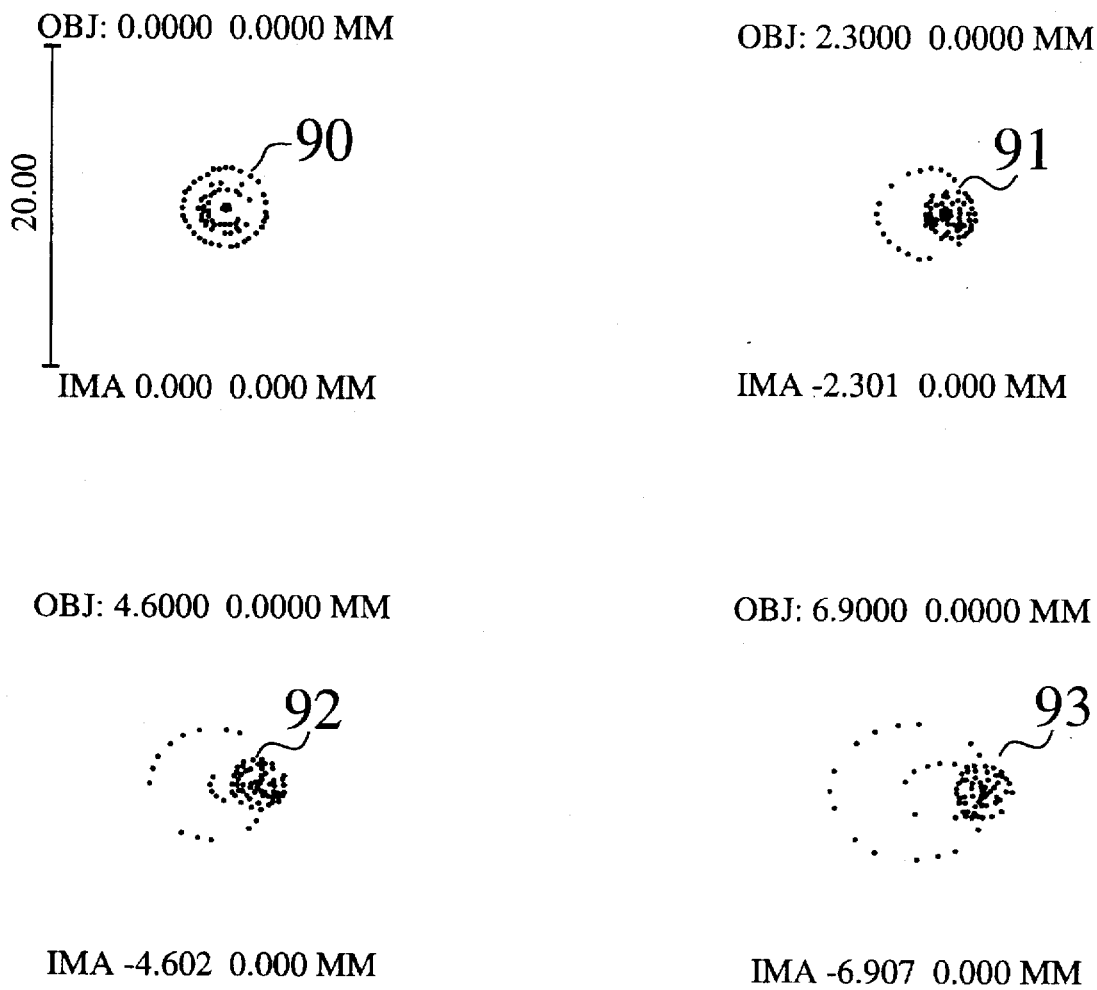
FIG. 9 is a spot diagram for the imaging system of FIGS. 8a and 8b.

FIG. 9 is a spot diagram for the imaging system of FIGS. 8a and 8b. As can be seen in the figure, the diameters of the spot diagrams 90, 91, 92, 93 produced by the four plate system are considerably smaller than those achieved with a three plate system, indicating that this system provides good compensation for aberrations introduced by imaging at an oblique angle through a transparent medium.

The invention greatly improves the image quality when imaging through a tilted plane parallel plate. The preexisting optical system remains rotationally symmetric except for the plates inserted therein. Such plane plates are readily manufacturable at reasonable cost, and they require only noncritical alignment within the system.

Although the invention is described herein with reference to the preferred embodiment, one skilled in the art will readily appreciate that other applications may be substituted for those set forth herein without departing from the spirit and scope of the present invention. For example, the imaged object may be located anywhere before the first plate. Accordingly, the invention should only be limited by the Claims included below.

What is claimed:

1. An apparatus for imaging through a planar transparent initial plate at an oblique viewing angle, comprising:

at least two additional plates of preferably similar thickness and material to that of said initial plate to provide compensation for off-center correction of more than one point, wherein said additional plates are tilted around tilt axes that are orthogonal to the optical axis of an imaging lens, and wherein said tilt axes are rotated around said optical axis with respect to each other.

2. The apparatus of claim 1, wherein each compensating plate n has the same tilt angle and has a tilt axis that is rotated by $\beta=i*360°/n$ with $i=0, 1, \ldots, n-1$ around the optical axis with respect to the initial plate.

3. The apparatus of claim 2, wherein each of the angles corresponding to different values of i is used, where i=0 is the trivial position of the initial plate.

4. The apparatus of claim 3, wherein the order in which the compensating plates are placed is not critical.

5. The apparatus of claim 1, comprising:

two compensating plates, wherein the compensating plates have their tilt axes rotated by 120° and 240°, and wherein the amount of rotation of each plate is substantially equal to said oblique viewing angle.

6. The apparatus of claim 1, comprising:

three compensating plates, wherein the compensating plates have their tilt axes rotated by 90°, 180°, and 270°, and wherein the amount of rotation of each plate is substantially equal to said oblique, viewing angle.

7. The apparatus of claim 1, wherein said compensating plates may be made from materials that include any of BK7, K5, silica, and low-fluorescent silica.

8. The apparatus of claim 1, wherein said initial plate is made from a different material than said compensating plates, and wherein appropriate thickness changes are made to the compensating plates to correct for differences between the refractive index of said initial plate and said compensating plates.

9. An apparatus for imaging through a planar, transparent initial plate at an oblique viewing angle, comprising:

at least two additional plates of preferably similar thickness and material to that of said initial plate to provide compensation for off-center correction of more than one point, wherein each additional plate n has the same tilt angle and has a tilt axis that is rotated by $\beta=i*360°/n$ with $i=0, 1, \ldots, n-1$ around the optical axis with respect to the initial plate, and, wherein each of the angles corresponding to different values of i is used, where i=0 is the trivial position of the initial plate.

10. The apparatus of claim 9, wherein the order in which the compensating plates are placed is not critical.

11. The apparatus of claim 9, comprising:

two compensating plates, wherein the compensating plates have their tilt axes rotated by 120° and 240, and wherein the amount of rotation of each plate is substantially equal to said oblique, viewing angle.

12. The apparatus of claim 9, comprising:

three compensating plates, wherein the compensating plates have their tilt axes rotated by 90°, 180°, and 270°, and wherein the amount of rotation of each plate is substantially equal to said oblique, viewing angle.

13. The apparatus of claim 9, wherein said compensating plates may be made from materials that include any of BK7, K5, silica, and low-fluorescent silica.

14. The apparatus of claim 9, wherein said initial plate is made from a different material than said compensating plates, and wherein appropriate thickness changes are made to the compensating plates to correct for differences between the refractive index of said initial plate and said compensating plates.

15. A method for imaging through a planar, transparent initial plate at an oblique angle, comprising the step of:

providing at least two additional plates of preferably similar thickness and material to that of said initial plate to provide compensation for off-center correction of more than one point, wherein each additional plate n has the same tilt angle and has a tilt axis that is rotated by $\beta=i*360°/n$ with $i=0, 1, \ldots, n-1$ around the optical axis with respect to the initial plate, and, wherein each of the angles corresponding to different values of i is used, where i=0 is the trivial position of the initial plate.

16. The method of claim 15, wherein the order in which the compensating plates are placed is not critical.

17. The method of claim 15, comprising the step of:

providing two compensating plates, wherein the compensating plates have their tilt axes rotated by 120° and 240, and wherein the amount of rotation of each plate is substantially equal to said oblique, viewing angle.

18. The method of claim 15, comprising the step of:
providing three compensating plates, wherein the compensating plates have their tilt axes rotated by 90°, 180°, and 270°, and wherein the amount of rotation of each plate is substantially equal to said oblique, viewing angle.

19. The method of claim 15, wherein said compensating plates may be made from materials that include any of BK7, K5, silica, and low-fluorescent silica.

20. The method of claim 15, wherein said initial plate is made from a different material than said compensating plates, and wherein appropriate thickness changes are made to the compensating plates to correct for differences between the refractive index of said initial plate and said compensating plates.

* * * * *